(12) United States Patent
Shimada et al.

(10) Patent No.: US 8,445,208 B2
(45) Date of Patent: May 21, 2013

(54) MULTIVARIATE ANALYSIS INVOLVING GENETIC POLYMORPHISMS RELATED TO MEDIATORS OF INFLAMMATORY RESPONSE FOR PREDICTION OF OUTCOME OF CRITCALLY ILL PATIENTS

(76) Inventors: Tadanaga Shimada, Chiba (JP); Shigeto Oda, Chiba (JP)

( * ) Notice: Subject to any disclaimer, the term of this patent is extended or adjusted under 35 U.S.C. 154(b) by 29 days.

(21) Appl. No.: 12/621,603

(22) Filed: Nov. 19, 2009

(65) Prior Publication Data

US 2010/0136562 A1    Jun. 3, 2010

Related U.S. Application Data

(60) Provisional application No. 61/116,780, filed on Nov. 21, 2008.

(51) Int. Cl.
*C12Q 1/68*    (2006.01)
(52) U.S. Cl.
USPC ............................ 435/6.11; 435/6.1; 435/6.17
(58) Field of Classification Search
None
See application file for complete search history.

(56) References Cited

U.S. PATENT DOCUMENTS 6,294,339 B1 *    9/2001    Wunderink et al. ......... 435/6.11

OTHER PUBLICATIONS

Nakada et al. Journal of Surgical Research. 2005. 129: 322-328.*
Watanabe et al. Critical Care Medicine.. 2005. 33(1): 89-97.*
de Jong et al. Genes and Immunity. 2002. 3: 25-29.*
Hirschhorn et al. Genetics in Medicine. vol. 4, No. 2, pp. 45-61, Mar. 2002.*
Lucentini et al. The Scientist (2004) vol. 18, p. 20.*
Wacholder et al. J. Natl. Cancer Institute (2004) 96(6):434-442.*
Ioannidis et al. Nature genetics (2001) 29:306-309.*
Halushka et al. Nature. Jul. 1999. 22: 239-247.*
Shimada et al. Cytokine, 2011. 54: 79-84.*

* cited by examiner

*Primary Examiner* — Carla Myers
(74) *Attorney, Agent, or Firm* — Kilyk & Bowersox, P.L.L.C.

(57)    ABSTRACT

A method of using genetic polymorphisms related to pro-inflammatory mediators to predict clinical outcome in critically ill patients admitted to an ICU is provided.

4 Claims, 2 Drawing Sheets

MULTIVARIATE ANALYSIS INVOLVING GENETIC POLYMORPHISMS RELATED TO MEDIATORS OF INFLAMMATORY RESPONSE FOR PREDICTION OF OUTCOME OF CRITCALLY ILL PATIENTS

This application claims the benefit under 35 U.S.C. §119 (e) of prior U.S. Provisional Patent Application No. 61/116,780, filed Nov. 21, 2008, which is incorporated in its entirety by reference herein.

FIELD

The present invention relates to the use of one or more genetic polymorphisms related to pro-inflammatory mediators as predictors to provide a more accurate prediction of the outcome in sick or critically ill patients, for instance, ones admitted to an ICU or other part of a hospital.

In the field of emergency and critical care medicine, a wide variety of investigations of the pathophysiology of critical conditions such as sepsis, trauma, and burn injury have been performed. In particular, the involvement of innate immunity in the pathophysiology of sepsis has been extensively investigated, and this research effort has revealed new findings clarifying the pathophysiology of sepsis (1). These findings have demonstrated that pathogen recognition by the innate immune system and subsequent production of pro-inflammatory mediators such as cytokines plays an important role in the pathophysiology of sepsis (2). These findings have also demonstrated the existence of individual differences in pathogen recognition and cytokine production, which might be associated with differences in genetic background (3). In fact, several gene-association studies have reported associations of particular genetic polymorphisms with clinical conditions in critically ill patients or their responses to particular types of treatment (4-6), suggesting the possibility personalized or tailor-made medicine based on genetic polymorphisms (7). On the other hand, investigations of the association of a particular genetic polymorphism in critically ill patients with outcome, severity of illness, and/or the duration of mechanical ventilation as a part of the attempt to identify genetic risk factors or predictors of outcome have yet to yield definitive conclusions (8-10).

The present inventors have previously reported associations of genetic polymorphisms with severity of illness and clinical outcome in septic patients (11, 12). A correlation was demonstrated between a genetic polymorphism and clinical outcome in patients with systemic inflammatory response syndrome (SIRS) and a Sequential Organ Failure Assessment (SOFA) score≧5 (12, 13). The possibility that genetic polymorphisms associated with outcome of critically ill patients can be used in combination with conventional clinical parameters such as disease severity and general condition to allow better prediction of the outcome of ICU patients, has not previously been explored.

The Acute Physiology and Chronic Health Evaluation (APACHE) II score (14) is an index typically used to measure the severity of disease of ICU patients. This point score, calculated as a sum of physiologic variables, age, and chronic health points for each ICU patient, is used not only to evaluate severity of disease but also as a prognostic predictor. While physiologic variables directly reflect the severity of disease, age and chronic health points are background factors contributing to disease severity. Besides the APACHE II score, factors such as gender, past medical history, and infection have been reported to influence the prognosis of ICU patients (15-18).

In many clinical conditions including sepsis, pancreatitis, trauma, and shock, organ failure in ICU patients resulting from aggravated inflammation is a factor of crucial importance in determining the clinical course and outcome of individual patients (19). The severity of illness in ICU patients increases with the number of failing organs, and various artificial organ support are employed depending on the number and type of failing organs. Associations between particular genetic polymorphisms and organ failure in critically ill patients have been frequently reported (20-22). Among the various types of organ failure noted in critically ill patients, acute lung injury has been examined most extensively to determine the relationship between this clinical condition and genetic polymorphisms of pro-inflammatory cytokines (23-25).

The possibility that genetic polymorphisms in ICU patients might influence not only their survival but also the number of failing organs and need for mechanical ventilation during their ICU stay, and the possibility that clinical course and outcome of ICU patients might depend not only on conventional demographic/clinical factors long known to be associated with them (i.e., APACHE II score, infection, age, gender, past medical history) but also on genetic factors associated with the same outcome measures (i.e., genetic polymorphisms involved in production of pro-inflammatory mediators), have not previously been explored.

REFERENCES

The references below and all publications mentioned herein are incorporated in their entirety by reference herein.
1. Akira S, Uematsu S, Takeuchi O: Pathogen recognition and innate immunity. Cell 2006; 124:783-801.
2. Cohen J: The immunopathogenesis of sepsis. Nature 2002; 420:885-891.
3. Arcaroli J, Fessler M B, Abraham E: Genetic polymorphisms and sepsis. Shock 2005; 24:300-312.
4. Barber R C, Chang L Y, Lemaire S M, et al: Epistatic interactions are critical to gene-association studies: PAI-1 and risk for mortality after burn injury. J Burn Care Res 2008; 29:168-175
5. Zhai R, Zhou W, Gong M N, et al: Inhibitor κB-α haplotype GTC is associated with susceptibility to acute respiratory distress syndrome in Caucasians. Crit Care Med 2007; 35:893-898
6. Calvano J E, Um J Y, Agnese D M, et al: Influence of the TNF-alpha and TNF-beta polymorphisms upon infectious risk and outcome in surgical intensive care patients. Surg Infect 2003; 4:163-169
7. Christie J D: The interleukin-6 gene and critical illness: is inflammatory gene variation the key to personalized medicine in the intensive care unit? Crit Care Med 2008; 36:1647-1649
8. Currier P F, Gong M N, Zhai R, et al: Surfactant protein-B polymorphisms and mortality in the acute respiratory distress syndrome. Crit Care Med 2008; 36:2511-2516
9. Walley K R, Russell J A: Protein C-1641 AA is associated with decreased survival and more organ dysfunction in severe sepsis. Crit Care Med 2007; 35:12-17.
10. Villar J, Pérez-Méndez L, Flores C, et al: A CXCL2 polymorphism is associated with better outcomes in patients with severe sepsis. Crit Care Med 2007; 35:2292-2297
11. Nakada T A, Hirasawa H, Oda S, et al: Influence of toll-like receptor 4, CD14, tumor necrosis factor, and inter- 11. leukine-10 gene polymorphisms on clinical outcome in Japanese critically ill patients. *J Surg Res* 2005; 129:322-328
12. Watanabe E, Hirasawa H, Oda S, et al: Cytokine-related genotypic differences in peak interleukin-6 blood levels of patients with SIRS and septic complications. *J Trauma* 2005; 59:1181-1189
13. Watanabe E, Hirasawa H, Oda S, et al: Extremely high interleukin-6 blood levels and outcome in the critically ill are associated with tumor necrosis factor- and interleukin-1-related gene polymorphisms. *Crit Care Med* 2005; 33:89-97
14. Kraus W A, Draper E A, Wagner D, et al: APACHE II: a severity of disease classification system. *Crit Care Med* 1985; 13:818
15. Mannino D M, Buist A S, Petty T L, et al: Lung function and mortality in the United States: data from the First National Health and Nutrition Examination Survey follow up study. *Thorax* 2003; 58:388-393
16. Egi M, Bellomo R, Stachowski E, et al: Blood glucose concentration and outcome of critical illness: the impact of diabetes. *Crit Care Med* 2008; 36:2249-2255
17. Mostafa G, Huynh T, Sing R F, et al: Gender-related outcomes in trauma. *J Trauma* 2002; 53:430-434
18. Vincent J L, Sakr Y, Sprung C L, et al: Sepsis Occurrence in Acutely Ill Patients Investigators.: Sepsis in European intensive care units: results of the SOAP study. *Crit Care Med* 2006; 34:344-353
19. Johnson D, Mayers I: Multiple organ dysfunction syndrome: a narrative review. *Can J Anaesth* 2001; 48:502-509
20. Barber R C, Chang L Y, Arnoldo B D, et al: Innate immunity SNPs are associated with risk for severe sepsis after burn injury. *Clin Med Res* 2006; 4:250-255
21. Chen Q X, Wu S J, Wang H H, et al: Protein C-1641A/-1654C haplotype is associated with organ dysfunction and the fatal outcome of severe sepsis in Chinese Han population. *Hum Genet* 2008; 123:281-287
22. Yende S, Quasney M W, Tolley E A, et al: Clinical relevance of angiotensin-converting enzyme gene polymorphisms to predict risk of mechanical ventilation after coronary artery bypass graft surgery. *Crit Care Med* 2004; 32:922-927
23. Nonas S A, Finigan J H, Gao L, et al: Functional genomic insights into acute lung injury: role of ventilators and mechanical stress. *Proc Am Thorac Soc* 2005; 2:188-194
24. Flores C, Ma S F, Maresso K, et al: IL6 gene-wide haplotype is associated with susceptibility to acute lung injury. *Transl Res* 2008; 152:11-17
25. Gao L, Flores C, Fan-Ma S, et al: Macrophage migration inhibitory factor in acute lung injury: expression, biomarker, and associations. *Transl Res* 2007; 150:18-29
26. American College of Chest Physicians/Society of Critical Care Medicine Consensus Conference: definitions for sepsis and organ failure and guidelines for the use of innovative therapies in sepsis. *Crit Care Med* 1992; 20:864-874
27. K/DOQI Clinical Practice Guidelines for Chronic Kidney Disease: Evaluation, Classification, and Stratification. *Am J Kidney Dis* 2002; 39:S1-S266
28. Ma P, Chen D, Pan J, et al: Genomic polymorphism within interleukin-1 family cytokines influences the outcome of septic patients. *Crit Care Med* 2002; 30:1046-1050
29. Oda S, Hirasawa H, Shiga H, et al: Sequential measurement of IL-6 blood levels in patients with systemic inflammatory response syndrome (SIRS)/sepsis. *Cytokine* 2005; 29:169-175
30. R Development Core Team: R: A language and environment for statistical computing. Vienna, Austria. R Foundation for Statistical Computing, 2007
31. Sablotzki A, Dehne M G, Friedrich I, et al: Different expression of cytokines in survivors and non-survivors from MODS following cardiovascular surgery. *Eur J Med Res* 2003; 8:71-76
32. Wilson A G, Symons J A, McDowell T L, et al: Effects of a polymorphism in the human tumor necrosis factor alpha promoter on transcriptional activation. *Proc Natl Acad Sci USA* 1997; 94:3195-3199
33. Louis E, Franchimont D, Piron A, et al. Tumor necrosis factor (TNF) gene polymorphism influences TNF-alpha production in lipopolysaccharide (LPS)-stimulated whole blood cell culture in healthy humans. *Clin Exp Immunol* 1998; 113:401-406
34. Kovar F M, Marsik C, Cvitko T, et al: The tumor necrosis factor alpha-308 G/A polymorphism does not influence inflammation and coagulation response in human endotoxemia. *Shock* 2007; 27:238-241
35. Stuber F, Udalova I A, Book M, et al: −308 tumor necrosis factor (TNF) polymorphism is not associated with survival in severe sepsis and is unrelated to lipopolysaccharide inducibility of the human TNF promoter. *J Inflamm* 1995; 46:42-50
36. Dianliang Z, Jieshou L, Zhiwei J, et al: Association of plasma levels of tumor necrosis factor (TNF)-alpha and its soluble receptors, two polymorphisms of the TNF gene, with acute severe pancreatitis and early septic shock due to it. *Pancreas* 2003; 26:339-343
37. Menges T, König I R, Hossain H, et al: Sepsis syndrome and death in trauma patients are associated with variation in the gene encoding tumor necrosis factor. *Crit Care Med* 2008; 36:1456-1462
38. El-Omar E M, Carrington M, Chow W H, et al: The role of interleukin-1 polymorphisms in the pathogenesis of gastric cancer. *Nature* 2000; 404:398-402
39. Barber R C, Chang L Y, Arnoldo B D, et al: Innate immunity SNPs are associated with risk for severe sepsis after burn injury. *Clin Med Res* 2006; 4:250-255
40. Frink M, Pape H C, van Griensven M, et al: Influence of gender and age on mods and cytokines after multiple injuries. *Shock* 2007; 27:151-156
41. Adrie C, Azoulay E, Francais A, et al: OutcomeRea Study Group: Influence of gender on the outcome of severe sepsis: a reappraisal. *Chest* 2007; 132:1786-1793
42. Choudhry M A, Bland K I, Chaudry I H: Trauma and immune response—effect of gender differences. *Injury* 2007; 38:1382-1391
43. Lam E, dos Santos C C: Advances in molecular acute lung injury/acute respiratory distress syndrome and ventilator-induced lung injury: the role of genomics, proteomics, bioinformatics and translational biology. *Curr Opin Crit Care* 2008; 14:3-10
44. Sutherland A M, Walley K R, Russell J A: Polymorphisms in CD14, mannose-binding lectin, and Toll-like receptor-2 are associated with increased prevalence of infection in critically ill adults. *Crit Care Med* 2005; 33:638-644
45. Balog A, Gyulai Z, Boros L G, et al: Polymorphism of the TNF-alpha, HSP70-2, and CD14 genes increases susceptibility to severe acute pancreatitis. *Pancreas* 2005; 30:e46-50.
46. García-Segarra G, Espinosa G, Tassies D, et al: Increased mortality in septic shock with the 4G/4G genotype of plasminogen activator inhibitor 1 in patients of white descent. *Intensive Care Med* 2007; 33:1354-1362

47. Manocha S, Russell J A, Sutherland A M, et al: Fibrinogen-beta gene haplotype is associated with mortality in sepsis. *J Infect* 2007; 54:572-577

SUMMARY

A feature of the present invention is to determine or predict clinical outcome of a patient who is seriously ill by collecting genomic DNA from the patient and detecting one or more genetic polymorphisms in the patient's genomic DNA. The genetic polymorphism can be a polymorphism involved in the production of pro-inflammatory mediators. The genetic polymorphism can comprise a G or A allele at position 308 of the TNF-α gene. The genetic polymorphism can comprise a C or T allele at position 31 of the IL-1β gene. The genetic polymorphism can comprise the RN1 allele with respect to a variable number of tandem repeats (VNTR) within intron 2 of the IL-1ra gene.

A method for determining or predicting the clinical outcome (or likelihood of that outcome) for a sick patient, or seriously ill patient such as one admitted to an intensive care unit ("ICU") is provided. The method can comprise collecting genomic DNA from the patient in order to detect one or more genetic polymorphisms in the patient's genomic DNA. The genetic polymorphism can be a polymorphism involved in the production of pro-inflammatory mediators. The genetic polymorphism can comprise a G or A allele at position −308 of the TNF-α gene. The genetic polymorphism can comprise a C or T allele at position −31 of the IL-1β gene. The genetic polymorphism can comprise the RN1 allele with respect to a variable number of tandem repeats (VNTR) within intron 2 of the IL-1 ra gene. Determining the clinical outcome for the patient can comprise the determination of a clinical factor. The clinical factor can be APACHE II score, infection, age, gender, and/or past medical history. Detecting the genetic polymorphism in the patient's genomic DNA can be accomplished by using an automated sequence detection system. Detecting the genetic polymorphism in the patient's genomic DNA can be accomplished by electrophoresis. Detecting the genetic polymorphism can comprise amplifying a gene comprising the polymorphism using an automated PCR thermal sequencer. The patient can have a clinical condition requiring intensive care. The clinical condition can be sepsis, trauma, severe acute pancreatitis, fulminant hepatitis, or be in a state of post-surgical recovery.

A method for determining or predicting the clinical outcome (or likelihood of that outcome) for a sick patient or seriously ill patient, such as admitted to an intensive care unit ("ICU"), can comprise collecting genomic DNA from the patient, detecting a genetic polymorphism in the patient's genomic DNA, determining that the clinical outcome for the patient is mortality, organ failure, and/or lung failure when the genetic polymorphism is detected and when a clinical factor is determined. The clinical factor can be APACHE II score, infection, age, gender, and/or past medical history. The clinical outcome can be ICU mortality, organ failure, and/or lung failure. The genetic polymorphism can comprise a G or A allele at position −308 of the TNF-α gene, the clinical factor can be APACHE II score, and the clinical outcome can be ICU mortality. The genetic polymorphism can comprise a C or T allele at position −31 of the IL-1β gene, the clinical factor can be APACHE II score, and the clinical outcome can be ICU mortality. The genetic polymorphism can comprise a G or A allele at position −308 of the TNF-α gene, a C or T allele at position −31 of the IL-1β gene, the clinical factor can be APACHE II score, and the clinical outcome can be ICU mortality. The genetic polymorphism can comprise the RN1 allele with respect to VNTR within intron 2 of the IL-1ra gene, the clinical outcome can be lung failure, and the clinical factor can be APACHE II score, past medical history, and/or infection. The past medical history can be heart disease.

BRIEF DESCRIPTION OF THE DRAWINGS

The present teachings will be described with reference to the accompanying drawings. The drawings are intended to illustrate, not limit, the present teachings.

DETAILED DESCRIPTION

Figure 1:
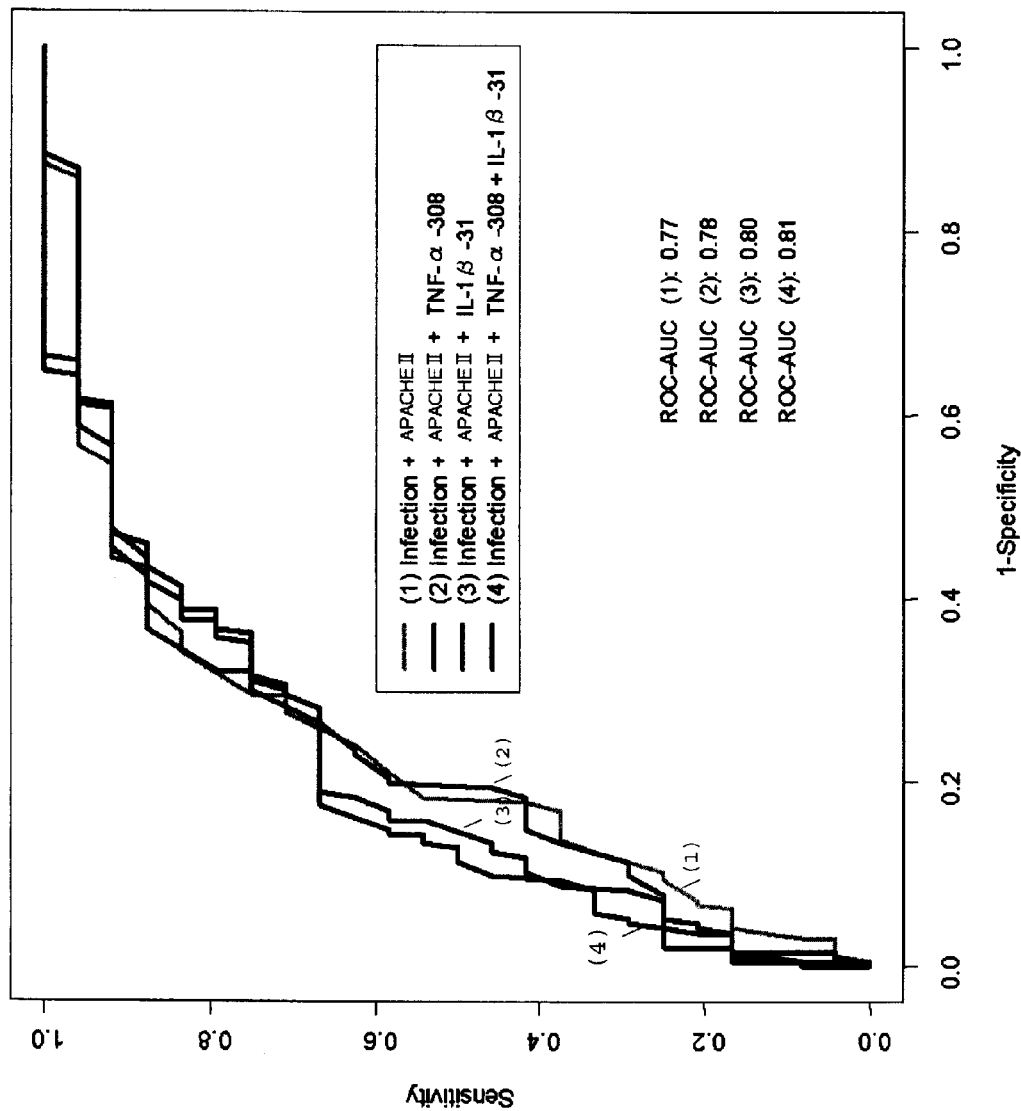
FIG. 1 shows ROC curves for prediction of mortality (e.s. ICU mortality) in the total patient group. Four different combinations of clinical and genetic parameters were used for the prediction. Curve 1: infection+APACHE II score (ROC-AUC=0.77); Curve 2: infection+APACHE II score+TNF-α-308 (ROC-AUC=0.78); Curve 3: infection+APACHE II score+IL-1β-31 (ROC-AUC=0.80); and Curve 4: infection+APACHE II score+TNF-α-308+IL-1β-31 (ROC-AUC=0.81).

The present invention and methods can be used to assist the medical industry in predicting the outcome of any patient who is sick or seriously ill. As an example, the present methods can be used in a hospital unit, such as an intensive care or trauma unit, to determine the clinical course or outcome of a seriously ill patient. There is no limitation as to where the invention can be used, and can include a nursing home, hospital, field hospital, and the like. The present invention can facilitate assessment of the seriousness of the patient's condition. By providing a better understanding of the seriousness of the patient's condition, the present invention can, for example, assist a caregiver, medical provider, or a relative of the patient, in making medical decisions, such as treatment decisions and end of life decisions.

The present invention shall be described in relation to an ICU, but it is to be understood that this is exemplary only, and the present invention applies to ill patients in any location. Genetic polymorphisms related to pro-inflammatory mediators can be significantly associated with the outcome of a patient who is sick or seriously ill. Thus, a genetic polymorphism can be used as a predictor of the outcome of a patient who is sick or seriously ill. The genetic polymorphism can be used alone, or in combination with other genetic polymorphisms and/or clinical factors conventionally used to predict patient outcome. For instance, the present inventors have found that, after a patient is admitted, for instance, to an ICU, the ICU patient's risk of death or ICU mortality can be determined based on one or more genetic factors and/or the combination of one or more genetic factors with clinical factors. One or more genetic factors, such as a genetic polymorphism, can allow the accurate prediction of the clinical course and outcome of ICU patients. The genetic polymorphism can be involved in production of pro-inflammatory mediators, such as cytokines. In addition or alternatively, the genetic polymorphism can be used to validate or further confirm a patient outcome predicted by conventional clinical factors.

The patient's genomic DNA can be collected and the clinical outcome of the patient can be determined based on the presence of the genetic polymorphism.

One or more genetic polymorphisms that are associated with pro-inflammatory mediators can include a single nucleotide polymorphism (SNPs) such as tumor necrosis factor-α (TNF-α)-308G/A, TNF-α-238G/A, LTα-T/C, interleukin-1β (IL-1β)-511A/G, IL-1β-31C/T, IL-6-174G/C, IL-6-634G/C, IL-10-1082A/G, IL-10-819C/T, IL-10-592C/A, macrophage migration inhibitory factor (MIF)-173G/C, CD14-159G/A, protein C (PROC)-1654C/T, PROC-1641G/A, and/or PROC-1476A/T. The genetic polymorphism can comprise the presence of a G or A allele at position −308. The genetic polymorphism can comprise the presence of a C or T allele at position −31 of the IL-1β gene. The genetic polymorphism can comprise the presence of the RN1 allele with respect to a variable number of tandem repeats (VNTR) within intron 2 of the IL-1ra gene. The clinical outcome of the patient can include the patient's chance of death or ICU mortality, the patient's chance of organ failure, and/or the patient's chance of lung failure. The patient can have a clinical condition requiring intensive care. The clinical condition can be sepsis, trauma, severe acute pancreatitis, fulminant hepatitis, and/or post-surgical recovery.

Other genetic polymorphisms can also be used, separately or in combination with one or more clinical factors to determine patient outcome.

The patient's clinical outcome can be determined based on one or more genetic factors and/or the combination of one or more genetic factors with clinical factors. The one or more genetic factors can be one or more genetic polymorphisms associated with the production of pro-inflammatory mediators. The genetic polymorphisms can be, for example, the presence of a G or A allele at position −308, the presence of a C or T allele at position −31 of the IL-1β gene, and/or the presence of the RN1 allele with respect to a variable number of tandem repeats (VNTR) within intron 2 of the IL-1ra gene. The clinical factors can be a high APACHE II score, infection, age, gender, and/or past diseases. Past diseases or past medical history can include various diseases, such as, heart disease, respiratory disease, liver disease, diabetes, malignancy, renal disease, and/or brain disease.

For instance, the clinical outcome of ICU mortality can be determined when the genetic polymorphism detected comprises the presence of a G or A allele at position −308 of the TNF-α gene, and/or the presence of a C or T allele at position −31 of the IL-1β gene. The clinical outcome of death is associated with an ICU score ranging from about 50-71, for example, 55-71, 65-71, or 70-71 (APACHE II score designated to the ICU patient). The clinical outcome of ICU mortality can be determined when the APACHE II score ranges from about 65-71 and when the genetic polymorphism detected comprises the presence of a G or A allele at position −308 of the TNF-α gene, and/or the presence of a C or T allele at position −31 of the IL-1β gene.

The clinical outcome of lung failure can be determined when the genetic polymorphism detected comprises the presence of the RN1 allele with respect to VNTR within intron 2 of the IL-1ra gene. The clinical outcome of lung failure can be determined when the genetic polymorphism detected comprises the presence of the RN1 allele with respect to VNTR within intron 2 of the IL-1ra gene, and when at least one of the following clinical factors is present, APACHE II ranging between 50-71, heart disease, and/or infection.

The patient's clinical outcome can be determined based on one or more genetic factors and/or the combination of one or more genetic factors with clinical factors. The present inventors have found that when clinical factors conventionally used to predict patient outcome are used in combination with genetic factors, a patient's clinical outcome can be determined more accurately than when clinical factors are used alone. In other words, when a patient has one or more particular genetic polymorphisms associated with a clinical outcome and falls within clinical parameters conventionally identified with the clinical outcome, the likelihood of occurrence of that particular clinical outcome is significantly greater than when clinical factors or parameters are considered alone. The term "significantly," as used herein, means that the predicted outcome is at least 50% (e.g., 50%-100%, 60%-90%, or 70%-80%) more accurate than without using the present invention. For example, it was found that two clinical factors (APACHE II score and infection) and one genetic factor (TNF-α-308) enabled more accurate prediction of mortality and that two clinical factors (APACHE II score and infection) and two genetic factors (TNF-α-308 and IL-1β-31) enabled even more accurate prediction of mortality.

A method for determining the clinical outcome for a patient for instance, admitted to an ICU, can comprise collecting genomic DNA from the patient and detecting the presence of one or more genetic polymorphisms associated with pro-inflammatory mediators in the genomic DNA. Collecting genomic DNA from the patient can be performed by any means known in the art. Genomic DNA can be collected from any biological sample from the patient. The biological sample can be blood, serum, urine, prostatic fluid, seminal fluid, semen, tissue extract sample, or biopsy. The biological sample can comprise, for example, collecting blood from the patient and extracting the genomic DNA from EDTA-anticoagulated whole blood. The relevant gene from the genomic DNA can be amplified using an automated polymerase chain reaction (PCR) thermal sequencer, or any other suitable method known in the art. Detection of the genetic polymorphisms associated with pro-inflammatory cytokines can be done using any sequence detection system known in the art. An automated sequence detection system, such as the ABI PRISM 7000 Sequence Detection System (Applied Biosystems, Foster City, Calif.), for example, can be used before and after PCR to detect each SNP. DNA fragments containing a variable number of repeat units in intron 2 of the IL-1ra gene can be amplified by PCR in a Bio-Rad iCycler (Bio-Rad Laboratories, Hercules, Calif.) and the resulting PCR products can be analyzed by electrophoresis in an Agilent Technologies Bioanalyzer 2100 (Agilent Technologies, Santa Clara, Calif.).

Two genetic polymorphisms, TNF-α-308GA and IL-1β-31CT/TT, can have significant association with ICU mortality in critically ill patients, particularly in those with sepsis. Combined use of genotypes at these two polymorphic loci with or without a conventional clinical predictor, can enable a more accurate prediction of outcome in ICU patients. A clinical predictor can be a high APACHE II score, gender, past medical history, and/or infection. Combined use of the genetic polymorphisms, TNF-α-308GA and IL-1β-31CT/TT with APACHE II score can have significant association with ICU mortality in critically ill patients.

EXAMPLE

The present teachings can be even more fully understood with reference to the example and resulting data that follow.
Materials and Methods
Study subjects. The subjects of the present study consisted of 224 patients admitted to the ICU of Chiba University Hospital between October 2001 and November 2007 with clinical conditions requiring intensive care such as sepsis, trauma, severe acute pancreatitis, fulminant hepatitis, and post-surgical recovery (patient group), and 294 healthy volunteers (control group).

Sepsis was diagnosed according to the criteria described in the consensus document by The American College of Chest Physicians/Society of the Critical Care Medicine Consensus Conference (26). The present study was approved by the Ethics Committee of the Chiba University Graduate School of Medicine. Informed consent was obtained from each study participant or his/her family member.

Data collection. Age, gender, and past medical history (cardiac, respiratory, liver, kidney, malignancy, diabetes, autoimmune, and brain diseases) were recorded for each patient on ICU admission to calculate the APACHE II score within 24 hours of ICU admission.

Clinical conditions recorded as past medical history. Clinical conditions to be recorded under "past medical history" included the following.

1) Heart disease: hypertension on medication, angina pectoris, ischemic heart disease, or New York Heart Association Class III/IV 2) Respiratory disease: chronic restrictive, obstructive, or vascular disease resulting in severe exercise restriction, i.e., unable to clime stairs or perform household duties; or documented chronic hypoxemia, hypercapnia, secondary polycythemia, pulmonary hypertension (>40 mmHg), or respirator dependency 3) Liver disease: Child classification B/C, biopsy-diagnosed cirrhosis, portal hypertension, or history of liver failure/hepatic coma 4) Diabetes: diabetes diagnosed at a medical institution and being treated with medication 5) Malignancy: malignancy of any type other than leukemia and lymphoma 6) Renal disease: chronic renal disease classified as Kidney Disease Outcome Quality Initiative (K/DOQI) Stage III or higher (27)

7) Brain disease: cerebral infarction, intracranial hemorrhage. Autoimmune diseases treated with immunosuppressants or high-dose steroids were excluded from "past medical history." Malignancies treated with chemotherapy or radiotherapy were also excluded from it.

Definition of outcome. ICU mortality and organ failure and lung injury during the ICU stay were considered outcome measures to be predicted in the present study. SOFA scores calculated during the ICU stay were used as an index of the severity of organ failure. SOFA scores were calculated on ICU admission and daily between 06:00-06:30 a.m. The maximum value of SOFA score during the ICU stay was designated SOFA max and a SOFA max>10 was considered to indicate severe organ failure. Use of a mechanical ventilation was recorded as an indicator of lung injury. Duration of mechanical ventilation exceeding seven days was considered to indicate severe lung injury.

Sample collection and DNA extraction. Blood samples were collected from the subject patients on ICU admission and once daily thereafter via arterial catheters. All of the daily blood samples were collected between 06:00-06:30 a.m. Venous blood samples were collected from healthy volunteers via an antecubital vein. Blood samples were collected in a blood collection tube containing ethylenediaminetetraacetic acid (EDTA) as anticoagulant. Genomic DNA was extracted from EDTA-anticoagulated whole blood using a QIAGEN QIAamp DNA Mini Kit (QIAGEN, Valencia, Calif.) according to the manufacturer's instructions.

Analysis of genetic polymorphisms. Sixteen different genetic polymorphisms related to cytokine production were investigated in the present study: single nucleotide polymorphisms (SNPs) at 15 different loci all located within the promoter region of the relevant gene and variable number of tandem repeats (VNTR) within intron 2 of the IL-1ra gene. The following SNP loci were examined: tumor necrosis factor-α (TNF-α)-308G/A, TNF-α-238G/A, LTα-T/C, interleukin-1β (IL-1β)-511A/G, IL-1β-31C/T, IL-6-174G/C, IL-6-634G/C, IL-10-1082A/G, IL-10-819C/T, IL-10-592C/A, macrophage migration inhibitory factor MIF-173G/C, CD14-159G/A, protein C (PROC)-1654C/T, PROC-1641G/A, and PROC-1476A/T.

Real-time polymerase chain reaction (PCR) assays with specific fluorescence-labeled probes were performed for genotyping of the 15 SNP loci. PCR primers and fluorogenic probes were designed for each SNP to be analyzed using PrimerExpress™ version 1.5 software (Applied Biosystems, Foster City, Calif.). Fluorescence in each well was measured before and after PCR using the ABI PRISM 7000 Sequence Detection System (Applied Biosystems, Foster City, Calif.). Details of the methods for SNP genotyping have been published previously (12).

The polymorphic region within intron 2 of the IL-1ra gene contains a variable number of 86-bp tandem repeat units. DNA fragments containing this region were amplified by PCR in a Bio-Rad iCycler (Bio-Rad Laboratories, Hercules, Calif.) and the resulting PCR products were analyzed by electrophoresis in an Agilent Technologies Bioanalyzer 2100 (Agilent Technologies, Santa Clara, Calif.). Alleles with four, two, five, three, and six 86-bp tandem repeat units (designated RN1, RN2, RN3, RN4, and RN5, respectively) yield amplification products that are 410 bp, 240 bp, 500 bp, 325 bp, and 595 bp in size, respectively, under the experimental conditions employed. Details of the methods for VNTR genotyping have been published previously (28).

Blood levels of IL-6. Blood levels of IL-6 in the ICU patients were assayed on ICU admission and once daily during the ICU stay by rapid chemiluminescense enzyme immunoassay (CLEIA) using an automated CLEIA system, Fujirebio Lumipulse $f^R$ (Fujirebio, Tokyo, Japan), equipped with a Fujirebio Human IL-6 CLEIA cartridge (Fujirebio, Tokyo, Japan) (12, 29). Plasma was immediately isolated from the blood samples collected as described under "Sample collection and DNA extraction" and stored frozen (−70° C.) until assay (12). The maximum blood level of IL-6 during the ICU stay was designated IL-6 Max.

Statistical analysis. Agreement of genotype frequencies with Hardy-Weinberg equilibrium was tested using a $\chi^2$ goodness of fit test for the control subjects and the patients. The difference in genotypic and allelic frequencies at each polymorphic locus between the patient and control groups was examined by $\chi^2$ test. Effects of APACHE II score, age, gender, past medical history, infection, and genetic polymorphism on ICU mortality, SOFA Max (>10), mechanical ventilation, and duration of mechanical ventilation (>7 days) in the total patient group (n=224) were examined by a stepwise multivariable logistic regression analysis applying a backward selection with a p-value of 0.05. Interaction between infection and other predictors were examined for each response variable. A similar analysis was performed for the sepsis subgroup (n=123). The predictive ability of each model was evaluated by a receiver-operating characteristics (ROC) curve and corresponding area under the curve (AUC), which were derived through leave-one-out cross-validation. All p values were two-sided; p-value less than 0.05 was considered statistically significant. All statistical analyses were performed using SAS ver 9.1.3 for Windows (SAS Institute, Inc., Cary, N.C.) and R ver. 2.6.1 for Windows (R Development Core Team) (30).

Results

Examining the effects of the 16 different genetic polymorphisms related to pro-inflammatory mediators and conventional demographic/clinical parameters (APACHE II score, age, gender, past medical history, and infection) on ICU mortality as well as disease severity (SOFA), mechanical ventilation, and duration of mechanical ventilation during ICU stay in the total patient group (n=224) by multivariate logistic regression analysis revealed factors significantly associated with ICU patient outcome. Subgroup analysis was performed in similar fashion in the sepsis subgroup (n=123). TNF-α-308GA (odds ratio, 8.01; 95% CI, 1.30-49.92; p=0.025), IL-1β-31CT (odds ratio, 3.25; 95% CI, 1.21-8.72; p=0.020), and APACHE II score (odds ratio, 1.08; 95% CI, 1.02-1.13; p=0.004) were significantly associated with ICU mortality in the total patient group. As described in more detail below, the factors significantly associated with ICU mortality in the sepsis subgroup were TNF-α-308GA (odds ratio, 12.92; 95% CI, 1.25-144.79; p=0.038), IL-1β-31CT/TT (odds ratio, 9.04; 95% CI, 1.12-72.75; p=0.039), and APACHE II score (odds ratio, 1.06; 95% CI, 1.01-1.12; p=0.030). The findings for the sepsis subgroup were thus similar to those for the total patient group. ROC analysis demonstrated that, compared with the combination of clinical parameters alone (APACHE II score and infection) (ROC-AUC=0.77), use of two clinical parameters and two genetic parameters (TNF-α-308 and IL-1β-31) enabled more accurate prediction of ICU mortality in the total patient group (ROC-AUC=0.81). Similarly, use of the two genetic parameters and APACHE II score (ROC-AUC=0.80) allowed more accurate prediction of ICU mortality in the sepsis subgroup compared with use of APACHE II score alone (ROC-AUC=0.68).

The 224 ICU patients studied included 123 patients with sepsis, 47 patients undergoing elective surgery (heart surgery, 25; abdominal surgery, 9; neuro/spinal surgery, 6; other, 4), 15 patients with severe acute pancreatitis, nine patients with trauma, six patients with cardiopulmonary arrest, five patients with autoimmune disease, four patients with respiratory disease, four patients with hemorrhagic shock, four patients with acute renal failure, three patients with acute drug intoxication, two patients with acute myocardial infarction, one patient with burn injury, and one patient with an acute abdomen. Table 1 summarizes the background characteristics of the total patient group and the sepsis subgroup.

TABLE 1

Background characteristics of the ICU patients studied

|  | Total (n = 224) | Sepsis (n = 123) |
|---|---|---|
| Age (years) | 59 (47.75-68.25) | 60 (51-69.5) |
| Sex (M:F) | 167:57 | 89:34 |
| ICU death (mortality, %) | 25 (11.16%) | 21 (17.07%) |
| ICU stay (days) | 7 (3-15.25) | 12 (5-22) |
| APACHE II score | 15.5 (11-22) | 18 (13.25-25) |
| SOFA Max | 8 (5-13) | 12 (8-15.75) |
| IL-6 Max (pg/mL) | 392 (118-6381) | 2915 (351-26405) |
| Past history |  |  |
| Brain | 7 (3.13%) | 3 (2.44%) |
| Cardiac | 55 (24.56%) | 19 (15.45%) |
| Respiratory | 7 (3.13%) | 3 (2.44%) |
| Chronic Renal Disease | 13 (5.80%) | 3 (2.44%) |
| Diabetes | 16 (7.17%) | 9 (7.32%) |
| Autoimmune | 15 (6.73%) | 11 (8.94%) |
| Malignant tumor | 33 (14.73%) | 22 (17.89%) |
| Hepatic failure | 16 (7.14%) | 10 (8.13%) |
| Mechanical ventilation | 146 (65.47%) | 91 (73.98%) |
| Duration of mechanical ventilation (days) | 3 (0-11) | 8 (2-18) |

Prior to the detailed analysis of the genetic polymorphisms in the ICU patient group, agreement of genotype frequencies with Hardy-Weinberg equilibrium was confirmed at all 15 SNP loci investigated in the present study in the control group. In addition, no significant difference in genotype frequency was observed between the patient and control groups with respect to any of the 16 genetic polymorphisms analyzed (data not shown).

Table 2 summarizes the results of SNP genotyping in the patient group. Of the 15 SNP loci analyzed, IL-6-174 was found to be monomorphic (Table 2). Three different genotypes were identified with respect to VNTR within intron 2 of the IL-1ra gene: RN1/1 in 197 patients, RN1/2 in 21 patients, and RN1/3 in six patients. Based on these findings, 15 different genetic polymorphisms (eliminating IL-6-174 from the 16 genetic polymorphisms examined) were investigated for association with clinical course and outcome of ICU patients.

TABLE 2

Genotypic and allelic frequencies of single-nucleotide polymorphisms in ICU patients

| Gene symbol | Alleles | Minor allele | Gene name | SNP ID | Chromosome location | Genotype frequency | Allele frequency |
|---|---|---|---|---|---|---|---|
| TNF-α -308 | G/A | A | Tumor necrosis factor | rs1800629 | 6p21.3 | GG:GA 215:8 | G:A 438:8 |
| TNF-α -238 | G/A | A | tumor necrosis factor | rs361525 | 6p21.3 | GG:GA 217:5 | G:A 441:7 |
| LT-α | T/C | C | lymphotoxin alpha | rs909253 | 6p21.3 | TT:TC:CC 83:114:26 | T:C 280:116 |
| CD14 -159 | G/A | A | CD14 molecule | rs2569190 | 5q22-q32; 5q31.1 | GG:GA:AA 56:100:68 | G:A 212:236 |
| IL-1β-31 | C/T | T | interleukin 1, beta | rs1143627 | 2q14 | CC:CT:TT 70:105:48 | C:T 245:101 |
| IL-1β-511 | A/G | G | interleukin 1, beta | rs16944 | 2q14 | AA:AG:GG 50:106:68 | A:G 206:242 |
| IL6 -634(572) | G/C | C | interleukin 6 | rs1800796 | 7p21 | GG:GC:CC 130:85:8 | G:C 345:101 |
| IL-6 -174 | G/C | C | interleukin 6 | rs1800795 | 7p21 | GG:GC 224:0 | G:C 448:0 |

TABLE 2-continued

Genotypic and allelic frequencies of single-nucleotide polymorphisms in ICU patients

| Gene symbol | Alleles | Minor allele | Gene name | SNP ID | Chromosome location | Genotype frequency | Allele frequency |
|---|---|---|---|---|---|---|---|
| IL-10 -592 | C/A | A | interleukin 10 | rs1800872 | 1q31-q32 | CC:CA:AA 100:92:32 | C:A 292:156 |
| IL-10 -819 | C/T | T | interleukin 10 | rs1800871 | 1q31-q32 | CC:CT:TT 100:93:31 | C:T 293:155 |
| IL-10 -1082 | A/G | G | interleukin 10 | rs1800896 | 1q31-q32 | AA:AG 204:20 | A:G 428:20 |
| MIF -173 | G/C | C | macrophage migration inhibitory factor | rs755622 | 22q11.23 | GG:GC:CC 12:73:138 | G:C 97:349 |
| PROC -1476 | A/T | T | protein C | rs1799810 | 2q13-q14 | AA:AT:TT 4:48:223 | A:T 56:390 |
| PROC -1641 | G/A | A | protein C | rs1799809 | 2q13-q14 | GG:GA:AA 4:48:169 | G:A 58:388 |
| PROC -1654 | C/T | T | protein C | rs1799808 | 2q13-q14 | CC:CT:TT 109:81:33 | C:T 229:147 |

Multivariable analysis revealed that three factors were significantly associated with ICU mortality in the total patient group: TNF-α-308GA (odds ratio, 8.01; 95% CI, 1.30-49.92; p=0.025), IL-1β-31CT (odds ratio, 3.25; 95% CI, 1.21-8.72; p=0.020), and APACHE II score (odds ratio, 1.08; 95% CI, 1.02-1.13; p=0.004). Infection was found to be associated with ICU mortality, although the association was not statistically significant (odds ratio, 3.22; 95% CI, 0.98-10.54; p=0.053). The factors significantly associated with ICU mortality in the sepsis subgroup were TNF-α-308GA (odds ratio, 12.92; 95% CI, 1.25-144.79; p=0.038), IL-1β-31CT/TT (odds ratio, 9.04; 95% CI, 1.12-72.75; p=0.039), and APACHE II score (odds ratio, 1.06; 95% CI, 1.01-1.12; p=0.030), indicating that the findings in the sepsis subgroup were similar to those in the total patient group (Table 3).

TABLE 3

Multivariate analysis of factors associated with ICU mortality

| | Parameter | Class | Odds ratio | 95% CI | p value |
|---|---|---|---|---|---|
| Total (n = 224) | TNF-α-308 | GA | 8.07 | 1.30-49.92 | 0.025 |
| | IL-1β-31 | CT | 3.24 | 1.21-8.72 | 0.019 |
| | APACHE II | 1 point | 1.08 | 1.02-1.13 | 0.004 |
| | Infection | + | 3.21 | 0.99-10.54 | 0.053 |
| Sepsis (n = 123) | TNF-α-308 | GA | 12.92 | 1.15-144.79 | 0.038 |
| | IL-1β-31 | CT | 9.04 | 1.12-72.76 | 0.039 |
| | APACHE II | 1 point | 1.06 | 1.01-1.12 | 0.030 |

APACHE, Acute Physiology and Chronic Health Evaluation;
CI, confidence interval

APACHE II score (odds ratio, 1.19; 95% CI, 1.12-1.25; p<0.001) and infection (odds ratio, 4.98; 95% CI, 2.47-10.05; p<0.001) were significantly associated with a SOFA max value>10 during the ICU stay in the total patient group. In the sepsis subgroup, APACHE II score (odds ratio, 1.16; 95% CI, 1.09-1.25; p<0.001) and female gender (odds ratio, 0.36; 95% CI, 0.14-0.91; p=0.03) were significantly associated with this outcome measure.

Four parameters were significantly associated with performance of mechanical ventilation in the total patient group: IL-1ra VNTR RN1/1 (odds ratio, 2.69; 95% CI, 1.01-7.18; p=0.048), history of heart disease (odds ratio, 3.28; 95% CI, 1.14-7.64; p=0.006), APACHE II score (odds ratio, 1.15; 95% CI, 1.10-1.22; p<0.001), and infection (odds ratio, 2.16; 95% CI, 1.09-4.38; p=0.028). In the sepsis subgroup, only APACHE II score (odds ratio, 1.06; 95% CI, 1.01-1.12; p=0.030) was significantly associated with this outcome measure (Table 4).

TABLE 4

Multivariate analysis of factors associated with mechanical ventilation

| | Parameter | Class | Odds ratio | 95% CI | p value |
|---|---|---|---|---|---|
| Total | IL-1ra | RN1/1 | 0.37 | 0.14-0.99 | 0.048 |
| | Heart | + | 3.29 | 1.41-7.64 | 0.006 |
| | APACHE II | 1 point | 1.15 | 1.10-1.22 | <0.001 |
| | Infection | + | 2.16 | 1.09-4.38 | 0.028 |
| Sepsis | APACHE II | 1 point | 1.06 | 1.01-1.12 | 0.030 |

APACHE II score (odds ratio, 1.11; 95% CI, 1.06-1.16; p<0.001) and infection (odds ratio, 9.28; 95% CI, 4.24-20.25; p<0.001) were significantly associated with duration of mechanical ventilation exceeding seven days in the total patient group. In the sepsis subgroup, only APACHE II score (odds ratio, 1.08; 95% CI, 1.03-1.14; p=0.002) was significantly associated with this outcome measure (Table 5).

TABLE 5

Multivariate analysis of factors associated with duration of mechanical ventilation >7 days

| | Parameter | Class | Odds ratio | 95% CI | p value |
|---|---|---|---|---|---|
| Total | APACHE II | 1 point | 1.11 | 1.06-1.16 | <0.001 |
| | Infection | + | 9.28 | 4.24-20.25 | <0.001 |
| Sepsis | APACHE II | 1 point | 1.08 | 1.03-1.14 | 0.002 |

Figure 2:
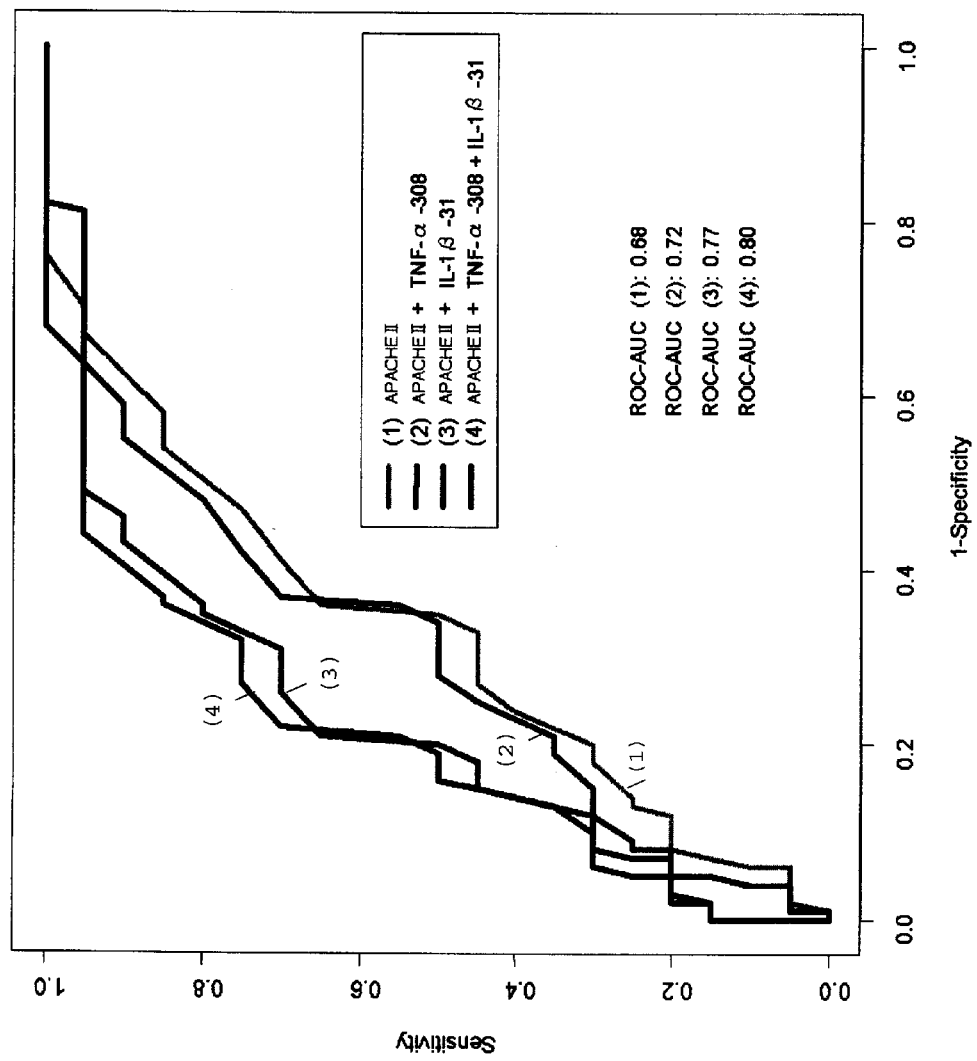
FIG. 2 shows ROC curves for prediction of ICU mortality in the sepsis subgroup. Four different combinations of clinical and genetic parameters were used for prediction. Curve 1: APACHE II score alone (ROC-AUC=0.68); Curve 2: APACHE II score+TNF-α-308 (ROC-AUC=0.72); Curve 3: APACHE II score+IL-1β-31 (ROC-AUC=0.77); and Curve 4: APACHE II score+TNF-α-308+IL-1β-31 (ROC-AUC=0.80).

The predictive ability of the model with different combinations of the four potential predictors of ICU mortality identified by multivariable analysis were evaluated by ROC analysis. Compared with the combination of clinical parameters alone (APACHE II score and infection) (ROC-AUC=0.77), the two clinical parameters plus one genetic parameter (TNF-α-308, ROC-AUC=0.78; IL-1β-31, ROC-AUC=0.80) enabled more accurate prediction of ICU mortality in the total patient group. Using two clinical parameters and two genetic parameters in combination enabled even more accurate prediction (ROC-AUC=0.81) (FIG. 1). These findings were obtained in the sepsis subgroup as well. Compared with APACHE II score alone (ROC-AUC=0.68), APACHE II score plus one genetic parameter (TNF-α-308, ROC-AUC=0.72; IL-1β-31, ROC-AUC=0.77) enabled more accurate prediction of ICU mortality. Use of two clinical parameters and two genetic parameters in combination enabled even more accurate prediction (ROC-AUC=0.80) (FIG. 2).

In accordance with the results described in the Example, TNF-α-308, IL-1β-31, and APACHE II score were independently associated with ICU mortality in both the total patient group and the sepsis subgroup. While the odds ratio for APACHE II score did not differ markedly between the total patient group (1.08) and the sepsis subgroup (1.06), that for TNF-α-308GA in the sepsis subgroup (12.92) was higher than that in the total patient group (8.01). Furthermore, the odds ratio for IL-1β-31CT/TT in the sepsis subgroup (9.04) was higher than that for IL-1β-31CT in the total patient group (3.25). These findings suggest that effects of genetic polymorphisms on ICU mortality might be greater in the sepsis subgroup than the total patient group.

The pivotal role of cytokines in the pathology of critically ill patients is now well recognized. Hypercytokinemia is now considered an index of severity of critical illness, and the progression of hypercytokinemia per se is known to play a role in aggravation of clinical condition (15, 31). In the present study, IL-6 Max during the ICU stay, an pro-inflammatory cytokine index, was significantly higher in the sepsis subgroup (Table 2, p<0.001), suggesting that hypercytokinemia in the sepsis subgroup may have been more severe than that in the total patient group. Consistent with this conclusion, APACHE II score and SOFA Max in the sepsis subgroup tended to be higher than those in the total patient group, indicating that the clinical condition was more severe in the sepsis subgroup than in the total patient group. Our previous findings suggested that some genetic polymorphisms related to overproduction of IL-6 and closely associated with clinical outcome in critically ill patients (12,13). This may explain the greater effects of two other genetic polymorphisms related to pro-inflammatory cytokines investigated in the present study, TNF-α-308 and IL-1β-31, on prediction of outcome in the sepsis group, which exhibited more severe hypercytokinemia and more severe clinical condition.

TNF-α has been the cytokine most extensively examined in studies of genetic polymorphism in septic patients. TNF-α-308G/A, a SNP within the promoter region of the TNF-α gene, is a typical functional genetic polymorphism of TNF-α. While the A allele at this SNP locus has been reported to be associated with increased transcription of the TNF-α gene in human B cells (32) as well as high production of TNF-α by circulating monocytes and granulocytes in humans under stimulation with bacterial lipopolysaccharide (LPS) (33), no significant association was observed between this SNP and TNF-α production in 87 healthy male volunteers receiving LPS infusion to induce experimental endotoxemia (34). The association of TNF-α-308G/A with sepsis, severe sepsis, and septic shock is thus still unclear. Stuber et al. (35) reported that no significant association between this SNP and incidence of severe sepsis was detectable in 80 patients who developed severe sepsis during post-surgical recovery. In contrast, Dianliang et al. (36) demonstrated an association between this SNP and incidence of septic shock in 208 patients with severe acute pancreatitis. Menges et al. (37) reported that this SNP was associated with incidence of sepsis and mortality in 159 patients with severe traumatic injury.

Also, the frequency distributions of genotypes (CC, CT, and TT) at IL-1β-31 and IL-1β-511 were almost the same, as indicated by the concordance rates of 98.2% and 97.7% in the patient group (Table 2) and control group (data not shown), respectively. The similar findings reported by El-Omar et al. (38) suggest that the patterns of inheritance of genotype at these two polymorphic loci within a population of a given ethnicity may be similar. Nevertheless, in the present Example, only IL-1β-31 was significantly associated with ICU mortality in both the total patient group and the sepsis subgroup, suggesting that these two polymorphisms might affect the clinical outcome of critically ill patients somewhat differently. Findings inconsistent with the present results have been obtained regarding the associations of IL-1β-31 and IL-1β-511 with sepsis: Barber et al. (39) reported no significant association of polymorphism at IL-1β-31 with risk of development of severe sepsis and mortality in 228 patients with severe burn injury, while Ma et al. (28) suggested that IL-1β-511 might be a risk factor for higher severity of sepsis in 60 ICU patients diagnosed with sepsis. It should be noted that neither of the two studies investigated these two genetic polymorphisms within the promoter region of the IL-1β gene simultaneously, as was done in the present Example.

APACHE II score and infection were factors associated with SOFA Max (>10) during the ICU stay in the total patient group, while APACHE II score and female gender were associated with this outcome measure in the sepsis subgroup. No significant association of genetic polymorphisms with SOFA Max during the ICU stay, an index of aggravation of clinical condition, was found in either the total patient group or the sepsis subgroup. Contrary to the finding in the sepsis subgroup (all aged over 50 years), recent findings supporting the influence of gender on outcome of critically ill patients frequently suggest a benefit of female gender (40-42): Frink et al. (40) demonstrated that, among patients with multiple traumatic injuries, females (not older than 50 years) were less susceptible to hypercytokinemia and multiple organ dysfunction syndrome (MODS) than age-matched males. Adrie et al. (41) reported that, among patients with severe sepsis, overall hospital mortality was significantly lower in women (>50 years old) than in age-matched men, with no significant difference between men and women in the younger group. Choudhry et al. (42) reviewed the differential effects of male and female gender steroids on post-traumatic immune response, and emphasized the role of estrogen in maintenance of immune function following injury via reversal of the suppressive effects of androgens. These findings, together with the findings of the present inventors, establish almost unequivocally the advantage of female gender with respect to survival and favorable recovery from traumatic injury.

Extensive investigations to identify genes associated with acute lung injury/acute respiratory distress syndrome and ventilator-associated lung injury have been documented, with a number of SNPs nominated as candidate disease-modifying loci (43). The results of the present Example show that, IL-1ra VNTR RN1/1 was the sole genetic marker significantly associated with mechanical ventilation in the total patient group, while none of the genetic polymorphisms examined was significantly associated with this outcome measure in the sepsis subgroup. In addition, no genetic polymorphism was significantly associated with duration of mechanical ventilation in either the total patient group or the sepsis subgroup. The RN2 allele of IL-1ra VNTR was significantly associated with mortality in septic patients, though the RN1 allele was not (28). Furthermore, IL-1ra VNTR per se is not included in the list of candidate disease-modifying genes in Lam and dos Santos (43).

The four potential predictors for ICU mortality were identified by multivariate analysis, two clinical parameters and two genetic parameters, were used in different combinations to predict mortality in the total patient group and the sepsis subgroup. ROC analysis revealed that, compared with the combination of clinical parameters alone (APACHE II score and infection), the two clinical parameters plus one or two genetic parameters enabled the more accurate prediction of ICU mortality in the total patient group (TNF-α-308GA and/or IL-1β-31CT). Consistent with this, APACHE II score plus one or two genetic parameters enabled more accurate prediction of ICU mortality in the sepsis subgroup than APACHE II score alone. However, the concomitant improvement of predictive power indicated by the change in ROC-AUC was greater in the sepsis subgroup (0.77 to 0.81 in the total patient group, 0.68 to 0.80 in the sepsis subgroup), suggesting that combined use of genetic parameters (genotypes of relevant polymorphic loci) with conventional clinical predictors (such as APACHE II score) will enable more accurate prediction of outcome in ICU patients with sepsis (TNF-α-308GA and IL-1β-31CT/TT).

In summary, the association of genetic polymorphisms in critically ill patients with ICU mortality, disease severity, performance of mechanical ventilation, and duration of mechanical ventilation was examined by multivariate analysis. Results demonstrated significant associations of two genetic polymorphisms, TNF-α-308G/A and IL-1β-31C/T, with ICU mortality in critically ill patients, particularly those with sepsis. The results further suggest that combined use of genotypes at these two polymorphic loci with a conventional clinical predictor, APACHE II score, enable a more accurate prediction of outcome in patients.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present teachings will be apparent to those skilled in the art from consideration of the present specification and practice of the present teachings disclosed herein. It is intended that the present specification and examples be considered as exemplary only.

What is claimed is:

1. A method for determining ICU mortality as a clinical outcome for a human sepsis patient, comprising:
   collecting genomic DNA from the human sepsis patient;
   detecting a presence or an absence of a genetic polymorphism at position −308 of the TNF-α gene and at position −31 of the IL-1β gene in the human sepsis patient's genomic DNA using a sequence detection system; and
   determining that the clinical outcome for the sepsis patient is ICU mortality when the genetic polymorphisms are detected and when a clinical factor is determined;
   wherein the genetic polymorphisms comprise the presence of a GA genotype at position −308 of the TNF-α gene, and the presence of a CT or TT genotype at position −31 of the IL-1β gene, and the clinical factor is an APACHE II score of 55 to 71.

2. The method of claim 1, wherein detecting the genetic polymorphisms comprises amplifying the TNF-α gene and the IL-1β gene using an automated PCR thermal sequencer.

3. The method of claim 1, wherein the sequence detection system comprises electrophoresis.

4. The method of claim 1, wherein the sequence detection system comprises an automated sequence detection system.

* * * * *

```
                              SEQUENCE LISTING

<160> NUMBER OF SEQ ID NOS: 15

<210> SEQ ID NO 1
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs1800629
<220> FEATURE:
<221> NAME/KEY: misc_feature
<222> LOCATION: (27)..(27)
<223> OTHER INFORMATION: r = a or g.

<400> SEQUENCE: 1
ggaggcaata ggttttgagg ggcatgrgga cggggttcag cctccagggt cc         52

<210> SEQ ID NO 2
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs361525
<220> FEATURE:
<221> NAME/KEY: misc_feature
<222> LOCATION: (27)..(27)
<223> OTHER INFORMATION: r = a or g.

<400> SEQUENCE: 2
tggcccagaa gacccccctc ggaatcrgag cagggaggat ggggagtgtg ag         52

<210> SEQ ID NO 3
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs909253
<220> FEATURE:
<221> NAME/KEY: misc_feature
<222> LOCATION: (27)..(27)
<223> OTHER INFORMATION: y = c or t.

<400> SEQUENCE: 3
agagacagga agggaacaga gaggaaycat ggcagaaaca gagaatgtgt ga         52
```

-continued

<210> SEQ ID NO 4
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs2569190
<220> FEATURE:
<221> NAME/KEY: misc_feature
<222> LOCATION: (27)..(27)
<223> OTHER INFORMATION: r = a or g.

<400> SEQUENCE: 4
caatgaagga tgtttcaggg aggggrccg taacaggaag gattctgcag gg        52

<210> SEQ ID NO 5
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs1143627
<220> FEATURE:
<221> NAME/KEY: misc_feature
<222> LOCATION: (27)..(27)
<223> OTHER INFORMATION: y = c or t.

<400> SEQUENCE: 5
agcctcctac ttctgctttt gaaagcyata aaaacagcga gggagaaact gg        52

<210> SEQ ID NO 6
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs16944
<220> FEATURE:
<221> NAME/KEY: misc_feature
<222> LOCATION: (27)..(27)
<223> OTHER INFORMATION: r = a or g.

<400> SEQUENCE: 6
ctaccttggg tgctgttctc tgcctcrgga gctctctgtc aattgcagga gc        52

<210> SEQ ID NO 7
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs1800796
<220> FEATURE:
<221> NAME/KEY: misc_feature
<222> LOCATION: (27)..(27)
<223> OTHER INFORMATION: s = c or g.

<400> SEQUENCE: 7
gatggccagg cagttctaca acagccsctc acagggagag ccagaacaca ga        52

<210> SEQ ID NO 8
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs1800795
<220> FEATURE:
<221> NAME/KEY: misc_feature
<222> LOCATION: (27)..(27)
<223> OTHER INFORMATION: s = c or g.

```
<400> SEQUENCE: 8 cactttttccc cctagttgtg tcttgcsatg ctaaaggacg tcacattgca ca        52

<210> SEQ ID NO 9
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs1800872
<220> FEATURE:
<221> NAME/KEY: misc_feature
<222> LOCATION: (27)..(27)
<223> OTHER INFORMATION: m = a or c.

<400> SEQUENCE: 9
ggaacacatc ctgtgacccc gcctgtmctg taggaagcca gtctctggaa ag        52

<210> SEQ ID NO 10
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs1800871
<220> FEATURE:
<221> NAME/KEY: misc_feature
<222> LOCATION: (27)..(27)
<223> OTHER INFORMATION: y = c or t.

<400> SEQUENCE: 10
ggtgtaccct tgtacaggtg atgtaayatc tctgtgcctc agtttgctca ct        52

<210> SEQ ID NO 11
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs1800896
<220> FEATURE:
<221> NAME/KEY: misc_feature
<222> LOCATION: (27)..(27)
<223> OTHER INFORMATION: r = a or g.

<400> SEQUENCE: 11
acaacactac taaggcttct ttgggarggg gaagtaggga taggtaagag ga        52

<210> SEQ ID NO 12
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs755622
<220> FEATURE:
<221> NAME/KEY: misc_feature
<222> LOCATION: (27)..(27)
<223> OTHER INFORMATION: s = c or g.

<400> SEQUENCE: 12
ccgctaagcc cggcgcaccg ctccaasctg ttctccactt ggcggctaga aa        52

<210> SEQ ID NO 13
<211> LENGTH: 52
<212> TYPE: DNA
<213> ORGANISM: homo sapiens
<220> FEATURE:
<221> NAME/KEY: misc_feature
```

```
<223> OTHER INFORMATION: partial sequence of SNP ID rs1799810
<220> FEATURE:
<221> NAME/KEY: misc_feature
<222> LOCATION: (27)..(27)
<223> OTHER INFORMATION: w = a or t.

<400> SEQUENCE: 13
caggctgtca tggcggcagg acggcgwact tgcagtatct ccacgacccg cc            52

<210> SEQ ID NO 14
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs1799809
<220> FEATURE:
<221> NAME/KEY: misc_feature
<222> LOCATION: (27)..(27)
<223> OTHER INFORMATION: r = a or g.

<400> SEQUENCE: 14
cctccctgct ggacggcatc cttggtrggc agaggtgggc ttcgggcaga ac            52

<210> SEQ ID NO 15
<211> LENGTH: 52
<212> TYPE: DNA
<213> ORGANISM: homo sapiens
<220> FEATURE:
<221> NAME/KEY: misc_feature
<223> OTHER INFORMATION: partial sequence of SNP ID rs1799808
<220> FEATURE:
<221> NAME/KEY: misc_feature
<222> LOCATION: (27)..(27)
<223> OTHER INFORMATION: y = c or t.

<400> SEQUENCE: 15
ttgccctcac ctccctccct gctggayggc atccttggtg ggcagaggtg gg            52
```